United States Patent [19]

Borsanyi

[11] Patent Number: 4,482,347

[45] Date of Patent: Nov. 13, 1984

[54] PERISTALTIC FLUID-PUMPING APPARATUS

[75] Inventor: Alexander S. Borsanyi, Newport Beach, Calif.

[73] Assignee: American Hospital Supply Corporation, Evanston, Ill.

[21] Appl. No.: 407,439

[22] Filed: Aug. 12, 1982

[51] Int. Cl.³ .............................................. A61M 5/00
[52] U.S. Cl. ........................... 604/153; 128/DIG. 12; 417/474
[58] Field of Search ............................ 128/DIG. 12; 604/151–153; 417/474, 475

[56] References Cited

U.S. PATENT DOCUMENTS

| | | | |
|---|---|---|---|
| 322,964 | 1/1966 | Roudaut | 103/149 |
| 1,874,667 | 8/1932 | Wada . | |
| 2,249,806 | 7/1941 | Bogoslowsky | 417/475 |
| 2,414,355 | 1/1947 | Bogoslowsky | 103/149 |
| 2,483,924 | 10/1949 | Moulinier | 604/153 X |
| 2,722,893 | 11/1955 | Maillot | 103/148 |
| 3,067,692 | 12/1962 | Brkich | 103/149 |
| 3,083,647 | 4/1963 | Muller | 103/148 |
| 3,233,553 | 2/1966 | Chanton | 103/149 |
| 3,609,069 | 9/1971 | Martinelli | 417/474 |
| 3,981,633 | 9/1976 | Wall | 417/474 |
| 3,990,444 | 11/1976 | Vial | 604/153 |
| 4,191,184 | 3/1980 | Carlisle | 128/214 |
| 4,201,525 | 5/1980 | Brown et al. | 417/477 |
| 4,373,525 | 2/1983 | Kobayashi | 417/474 X |

Primary Examiner—Dalton L. Truluck
Attorney, Agent, or Firm—Tilton, Fallon, Lungmus

[57] ABSTRACT

An apparatus comprising a compact, portable peristaltic pump particularly suitable for medical use in infusing or removing fluids. The pump includes a series of small bearing assemblies each having concentric inner and outer members capable of free rotation with respect to each other. The inner members are eccentrically mounted upon a power-driven shaft with their centers arranged in a helix about the axis of the shaft. A thin elastomeric membrane is disposed along the series of bearing assemblies with the outer members having their surfaces tangentially engaging one side of the membrane along a first band or linear zone of contact. An elastomeric tube extends along the opposite side of the membrane, engaging that membrane along a second band or linear zone of contact directly opposite the first band of contact. A platen supports the tube so that the membrane is in constant engagement with the tube along the second band of contact, and is in either constant or periodically-interrupted engagement with the bearing assemblies along the first band of contact, during pumping operation. The disclosure also sets forth embodiments in which the membrane is preferentially reinforced and in which the apparatus includes a fluid container and a suitable patient connector for administering or removing parenteral and biological fluids.

35 Claims, 17 Drawing Figures

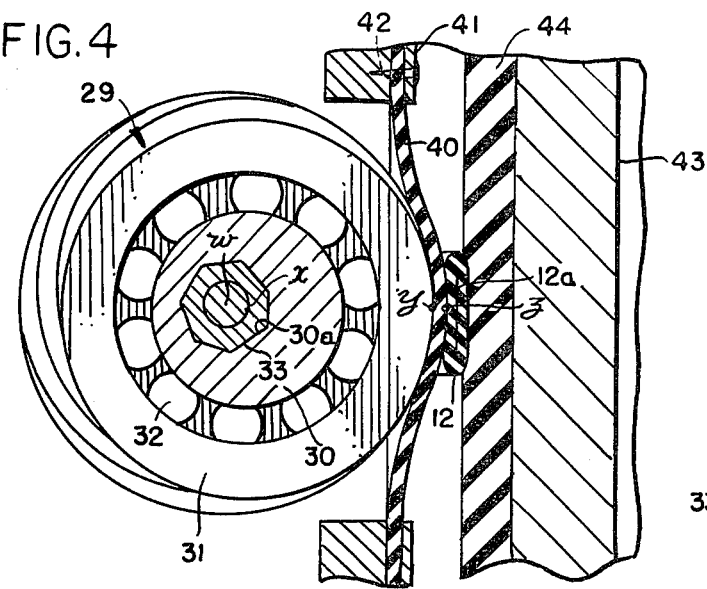
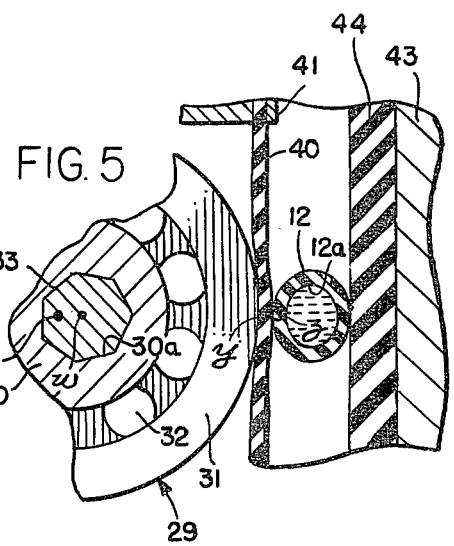
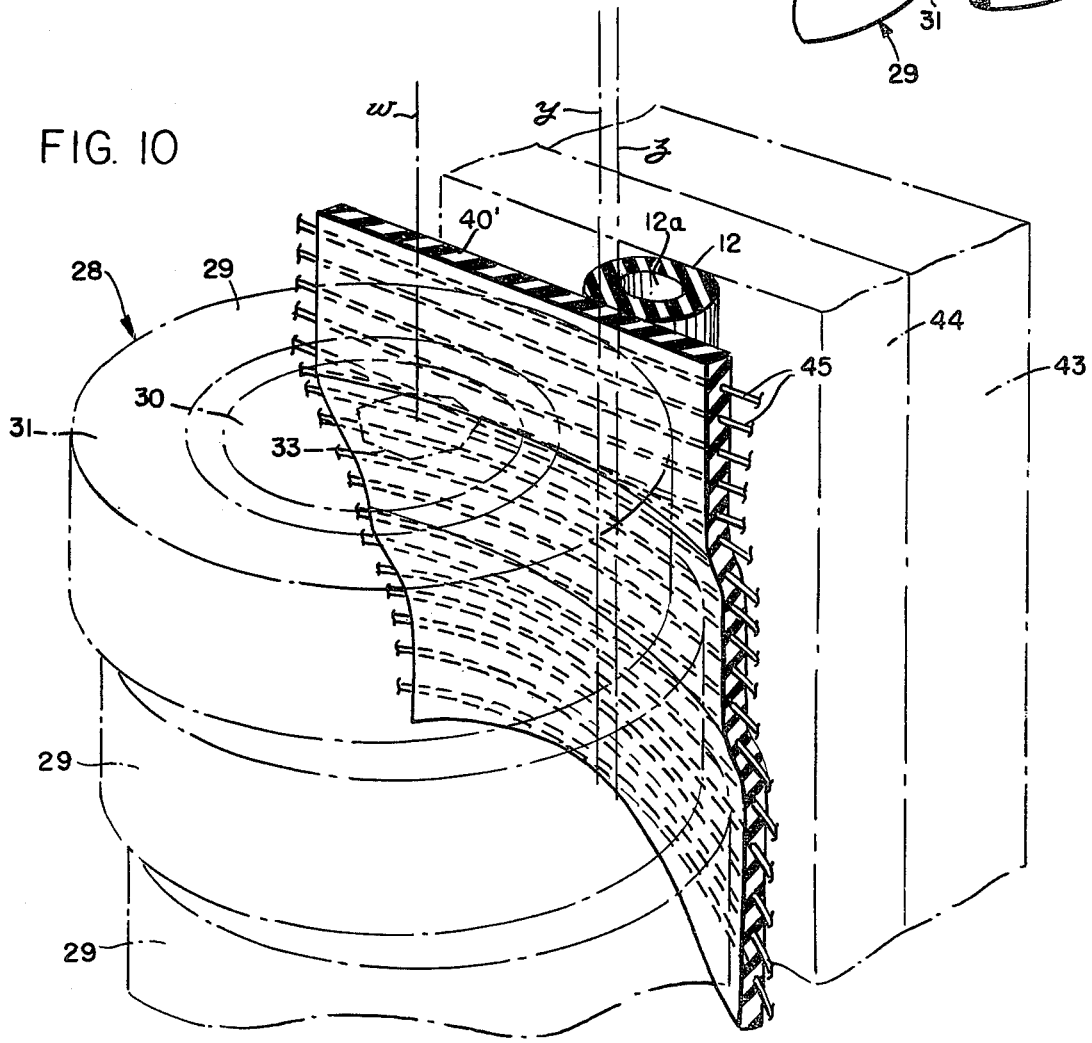

PERISTALTIC FLUID-PUMPING APPARATUS

BACKGROUND

Muller U.S. Pat. No. 3,083,647 discloses a fluid metering and pumping device in which a multiplicity of pressure bars driven by a camshaft with offset eccentrics progressively collapse a tube to produce a peristaltic advancement of fluid through that tube. While such a system might be effective for tubing having an inside diameter (ID) of 0.20 inches or more, the size and complexity of the apparatus would tend to be objectionable even for such an application. Such complexity—the numerous parts and their assembly—would become prohibitive if such a system were to be used with relatively small-size tubing (i.e., below 0.1 inches ID) and if the dimensions of the pump were to be kept to a minimum. Miniaturization could be achieved only with considerable effort and expense and at the risk of performance variations and uncertainties that would make such an apparatus unsuitable as a pump for metering medical or biological fluids.

Other patents such as Roudaut U.S. Pat. No. 3,229,643, Wall U.S. Pat. No. 3,981,633, and Chanton U.S. Pat. No. 3,233,553 disclose somewhat similar pumps in which the shafts and eccentrics are disposed internally rather than externally in relation to the flexible tubes. Such systems avoid some of the complexities and inherent problems associated with the pressure bar system disclosed by Muller; however, they present other problems that tend to exclude their use in medical systems or in any other systems where low-volume pumping at predetermined flow rates, in a precise and reliable manner, is deemed essential. It is also apparent that replacement of the tubing, as well as cleaning and sterilization of the fluid-contacting components so that the pumps might be used successively by the same or different patients, would be extremely difficult if not impossible.

Other patents illustrative of the state of the art are U.S. Pat. Nos. 3,067,692, 2,722,893, 1,874,667, 2,414,355, and 2,249,806.

SUMMARY OF THE INVENTION

An important aspect of this invention lies in recognizing that the complexities, inaccuracies, and other deficiencies of prior constructions may be overcome by interposing a thin elastomeric membrane directly between a resilient tube and a series of eccentrically-mounted bearing assemblies so that the outer races or members of the bearing assemblies and the resilient tube frictionally engage opposite sides of the membrane along parallel bands or linear zones of contact, but with the membrane nevertheless isolating and protecting the tube against contact with the bearing assemblies. The contact between the membrane and tube is continuous, whereas the contact between the membrane and each bearing assembly may either be continuous or interrupted for a short angular distance with each revolution of the pump shaft. In either case, the membrane protects the tube against lateral stresses that might cause lateral displacement or unintentional lateral deformations that would adversely affect reliable performance of the pump. In addition, the membrane reduces the possibility of damage or wear to the tube by the bearing assemblies and protects the mechanism against fluid contact when, for example, a tube is being removed and replaced. Because the pump mechanism is completely external to the tube, the tube may be readily replaced and may be supplied as a disposable item for one-time use, a particularly important consideration where the pump apparatus is intended for medical use.

The tube is braced or supported by a rigid platen which may be formed of transparent material to permit inspection of the tube during pump operation. Ideally, the platen is provided with a layer of resilient material in contact with the tube to reduce the torque peaks during pump operation, thereby permitting the use of a smaller less-powerful motor to drive the pump shaft, and to facilitate leaktight peristaltic occlusion of the tubing during pump operation. Like the platen, the resilient layer or liner may be formed of a material sufficiently transparent to permit observation of pump operation therethrough.

In one embodiment of the invention, the elastomeric membrane may be reinforced to resist planar stretching in transverse directions, that is, in directions lying in the plane of the membrane perpendicular to the band of contact between the membrane and the elastomeric tube. Such reinforcement may take the form of laterally-extending parallel filaments embedded within the membrane and formed of flexible but substantially non-stretchable material.

The result is a pump apparatus characterized by compactness, simplicity of construction, and precise, accurate, reliable operation. Such characteristics make it particularly suitable for medical use in a fluid infusion or administration system, including drug delivery, or in a system for withdrawing fluids, such as wound, urine, pleura, or other drainage systems. The construction and operation of the pump apparatus permits miniaturization to such an extent that, for example, the pump may be one component of an inconspicuous wearable infusion system that may be readily concealed within a belt or other article of clothing for continuous administration of insulin to a diabetic patient.

Other features, objects and advantages of the invention will become apparent from the drawings and specification.

DRAWINGS

FIG. 4 is a still further enlarged horizontal sectional view taken along line 4—4 of FIG. 3 and showing the eccentric bearing assembly in an extreme position compressing and occluding the elastomeric tube.

FIG. 5 is a horizontal sectional view similar to FIG. 4 but showing the bearing assembly in its outer extreme position with the elastomeric tube nearly fully expanded.

FIG. 10 is a fragmentary perspective view of the apparatus modified to include a membrane pereferentially reinforced against stretching in directions transverse to the axis of the tube.

DETAILED DESCRIPTION

Figure 1:
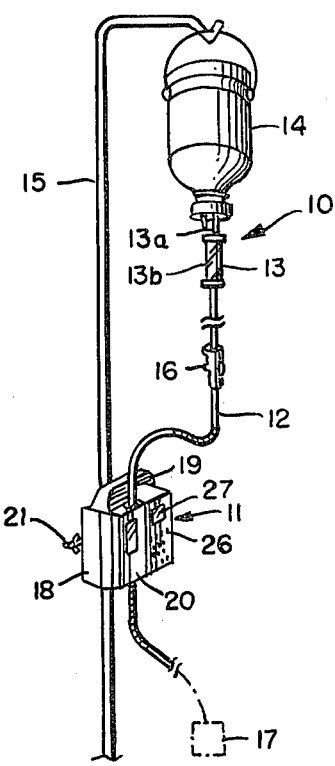
FIG. 1 is a perspective view of a system utilizing the peristaltic fluid-pumping apparatus of the invention for metered intravenous (IV) administration.

Referring to the drawings, and particularly to FIGS. 1-9, the numeral 10 generally designates an apparatus including a metering pump 11, a fluid delivery tube 12, coupling means 13 for coupling one end of the tube to a suitable container 14, in this case a parenteral solution container supported by a conventional IV stand 15. The coupling means takes the form of a spike 13a formed as part of drip chamber housing 13b and received within the opening of a vent-providing stopper at the mouth of the container. A suitable valve or clamp 16 may be provided for controlling or interrupting the flow of fluid through tube 12.

Figure 2:
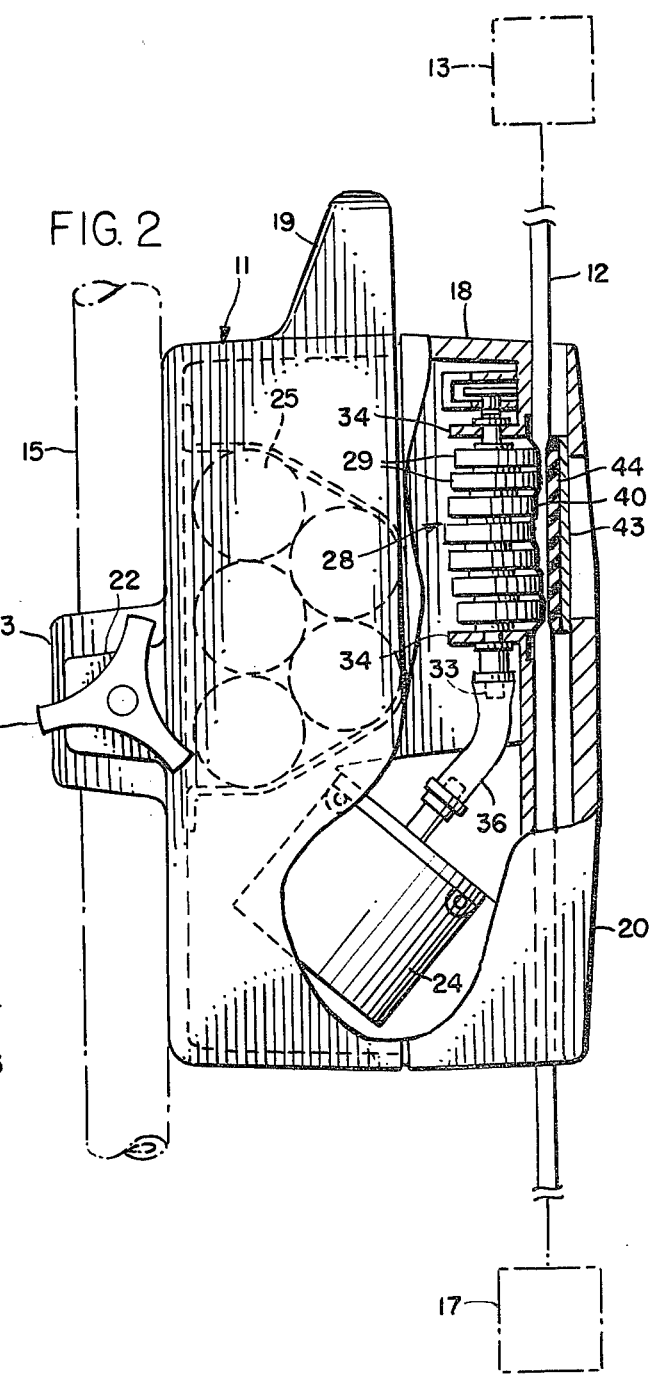
FIG. 2 is a side elevation taken partly in section showing the pump apparatus.

The opposite end of the tube 12 leads to a suitable connector 17 represented diagramatically in FIGS. 1 and 2. In the case of a fluid administration system, the connector would ordinarily take the form of a hypodermic needle or cannula. Excluding metering pump 11, the elements of the system shown in FIGS. 1-2 are conventional and well known and, therefore, further discussion of such elements is believed unnecessary herein.

The metering pump 11 includes a housing 18 equipped with a handle 19 and a door or removable panel 20. Attachment of the housing to IV stand 15 is achieved by thumb screw 21 which can be tightened against the pole of the stand when the pole extends between a pair of ears 22, 23 projecting from the rear of the housing. An electric stepping motor 24 drives the pump and a power pack 25 composed of one or more batteries or power cells (5 are shown) is located within the housing to supply power for the motor and other components. The electrical controls for the operation of the motor may be simple or complex depending on the requirements and use of the system. In the illustration given, a plurality of finger buttons 26 are provided at the face of the housing and a digital display window 27 reveals information concerning selected delivery rates as controlled by motor speed for a tube 12 of selected cross sectional dimensions.

The pump mechanism 28 includes a series of bearing assemblies 29 each having inner and outer bearing members 30 and 31, respectively. Preferably the inner member 30 takes the form of an inner bearing race, the outer member 31 constitutes an outer race, and anti-friction bearing elements 32 are disposed therebetween. Such anti-friction bearing elements would normally consist of ball bearings; however, the use of various types of roller bearings is possible. Furthermore, other types of bearing assemblies, such as self-lubricating sleeve bearings, might be advantageously used.

Figure 3:
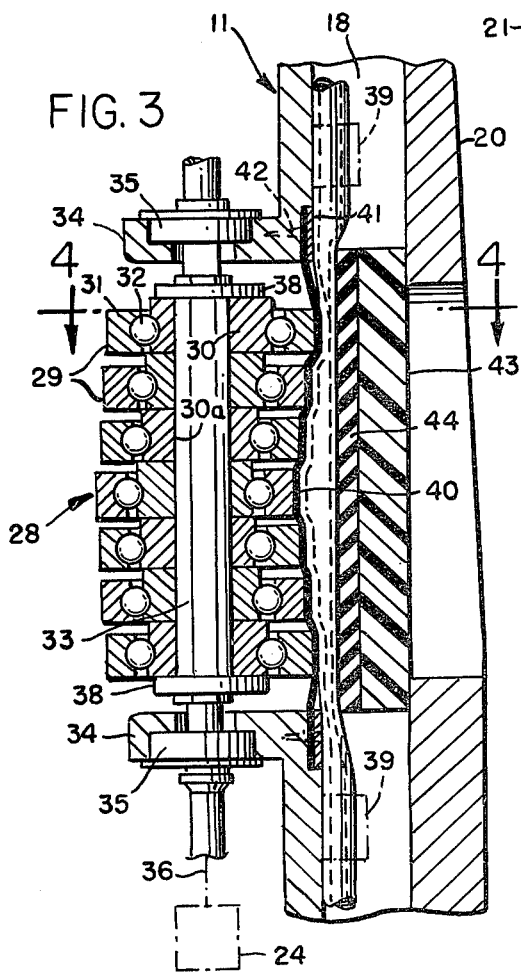
FIG. 3 is an enlarged vertical sectional view showing details of the apparatus.

Each inner race (or member) is mounted eccentrically upon a drive shaft 33. Journalling means in the form of hangers 34 and bearings 35 (preferably ball bearings) support the ends of drive shaft 33 as shown in FIGS. 2 and 3. One end of the shaft (the lower end in the embodiment illustrated) is operatively connected to motor 24. A flexible coupling 36 is shown for that purpose, but other connecting means may be used. Also, while the drive shaft 33 is illustrated with its longitudinal axis oriented vertically, it is to be understood that the action of the pump is independent of such orientation as long as fluid is available to the pump through line or tube 12.

Each inner race (or member) 30 is eccentrically mounted upon shaft 33 with the centers of all such races being equidistant from the axis w of the drive shaft and with the angular spacing between all of such centers being essentially the same and the sum of the angular spacing being 360°. Where a series of seven bearing assemblies is provided as shown, the incremental angular distance between the centers of the inner races should be 360° divided by seven, or approximately 51.43°. A greater or smaller number of bearing assemblies may be provided, although the preferred range is believed to be 3 to 30 such assemblies. Of particular importance is the fact that the series of bearing assemblies must be mounted upon the drive shaft 33 so that the centers x of the inner races describe a spiral or helix of at 360° about drive shaft axis w.

The inner races 30 may be secured upon the shaft 33 in any suitable manner. In the embodiment illustrated in the drawings, shaft 33 has a central portion of non-circular (heptagonal) cross sectional outline and the eccentrically-disposed openings 30a in the respective inner races 30 are of the same configuration so that the eccentric bearings may be incrementally positioned upon the shaft with their centers helically oriented. The inner races are thereby secured against independent relative rotation with respect to shaft 33, and locking elements 38 are secured to the shaft at opposite ends of the series of bearing assemblies 29 to hold the series against axial displacement.

The central portion of elastomeric tube 12 is supported with its longitudinal axis parallel with the rotational axis of the shaft 33 and with a linear zone of the outer surface of a membrane 40 in contact with the outer surfaces of outer races 31. Ideally the tube is stretched so that it is under slight axial tension, thereby assuring that the portion of the tube opposite the bearing assemblies will be straight or linear in the absence of lateral distorting forces. For purposes of such tensioning, and to insure parallel alignment of the tube with the axis w of the drive shaft, mounting straps or brackets may be located at 39 to immobilize those portions of the tube with respect to housing 18. Alternatively, such portions of the tube may be secured to the housing by adhesives or by any other suitable means.

The elastomeric imperforate membrane 40 is interposed between tube 12 and the cylindrical surfaces of outer bearing members or races 31, as shown most clearly in FIGS. 3-5. The membrane is planar in an untensioned state and assumes the configuration shown in FIG. 3 because of the distortions developed by bearing assemblies 29 and tubing 12. It bridges the space in which the series of bearing assemblies is located and separates that mechanism from tube 12. Any suitable means may be used to secure the periphery of the membrane to casing or housing 18; in the embodiment illustrated, a frame 41 is secured to the housing by screws 42 and clamps the perimeter of the membrane tightly in place.

A rigid platen 43 braces tube 12 and not only maintains the tube in contact with one surface of the membrane 40 but also maintains the opposite surface of the membrane in contact with the outer races of the bearing assemblies 29. More specifically, as shown in FIGS. 4 and 5, the outer races tangentially engage the membrane 40 along a first linear zone or band of contact y, and the elastomeric tube engages the opposite side of the membrane along a second linear zone or band of contact z directly behind or opposite from the first band of contact. Also, the two bands of contact y and z lie in the same plane as the rotational axis w of drive shaft 33.

Each bearing assembly 29 has its inner race 30 eccentrically mounted so that its center x moves between one extreme position in which center x is spaced maximally from the platen and the lumen 12a of the tube is substantially fully open (FIG. 5) and the other extreme position in which center x is spaced minimally from platen 43 and the lumen of the tube is closed (FIG. 4). To reduce torque peaks that develop as each bearing assembly sweeps through the tube-occluding position of FIG. 4, especially when two such assemblies (the first and last of the series) simultaneously compress and substantially close the tube, platen 43 may be provided with a resilient facing 44 engaging and supporting tube 12. The facing must not be so compliant that it will allow outward displacement of the tube in preference to complete occlusion of that tube. The tube should close as shown in FIG. 4 with the resilience of facing 40 serving the primary purpose of reducing the torque peak once such occlusion has taken place. Additionally, the resilient facing may perform the secondary function of providing additional resistance to lateral or transverse displacement of the portion of the tube 12 extending alongside the series of bearing assemblies 29 and membrane 40. In general, a facing material having a durometer of about 60 to 80 has been found effective.

Lateral displacement of the tube during pump operation is prevented primarily by membrane 40 and by the effectiveness of anti-friction bearing elements 32. A slight frictional resistance is necessarily inherent in the operation of each bearing assembly 29, but that resistance is substantially less than the frictional resistance between the outer surface of outer race 31 and the surface of membrane 40 in contact therewith. Tangential sliding movement between the outer races of the bearing assemblies and membrane 40 is therefore avoided. Since the membrane's resistance to stretching is substantial in relation to the frictional resistance inherent in the operation of the bearing assembly, rotational forces that might otherwise be transmitted to tube 12 are isolated by membrane 40.

In the form of the invention depicted in FIGS. 2–5, each outer race 31 remains in continuous contact with membrane 40 even when the center x of bearing assembly 29 is spaced maximally from the platen and the lumen of tube 12 is substantially fully open (FIG. 5). Alternatively, the apparatus may be adjusted or constructed so that it is structurally and functionally identical to what has already been described except that the outer race of each bearing assembly is momentarily drawn out of contact with the membrane when the shaft has rotated to space center x its maximum distance from the platen, in which case the outer race will be free to rotate a limited angular distance (i.e., 360° divided by the number of assemblies) until it is again brought into contact with the membrane. Such an embodiment not only provides the advantages of allowing the tube to expand to a fully open position (in which the cross section of the lumen is circular in outline) but also, by permitting incremental rotation of the outer race, tends to produce more uniform bearing wear and thereby increase the operating life of the apparatus.

The operation of such a modified version of the pump is schematically illustrated in FIGS. 6–9. The two concentric circles represent a bearing assembly 29 with the inner circle indicating the inner race or member 30 and the outer circle representing the outer race or member 31. The inner race is eccentrically mounted with the extent of eccentricity being the distance between the center x of the inner race and the rotational axis w of the mounting shaft.

Figure 7:
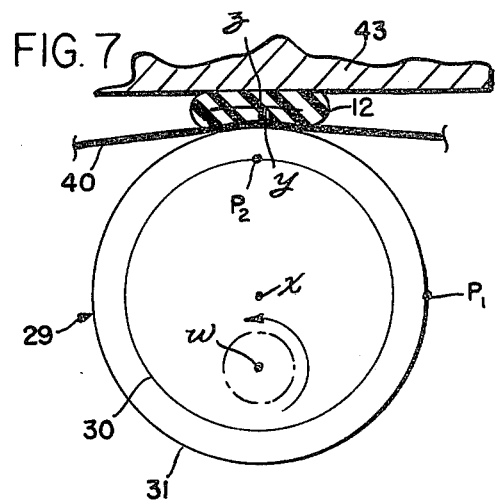
Figure 8:
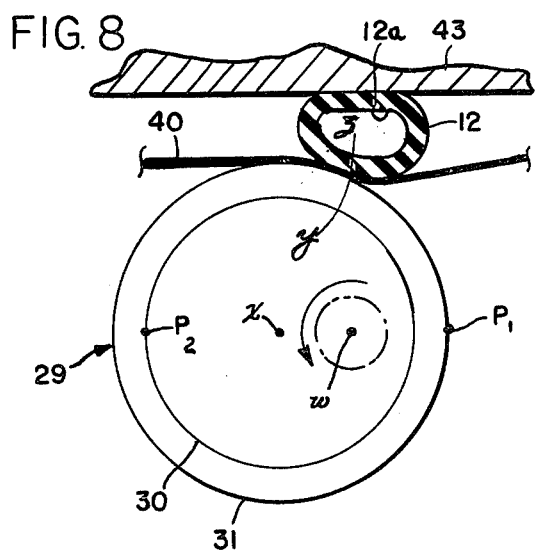
Figure 9:
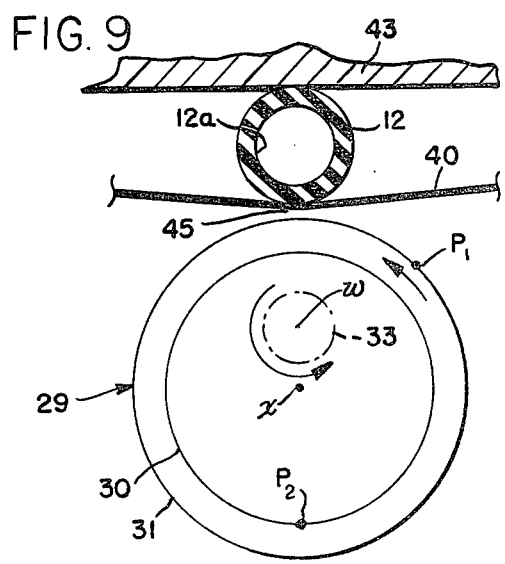

The linear zone or band of contact z between tube 12 and membrane 40 is clearly shown in FIGS. 6–9. Similarly, the linear zone or band of contact y between the membrane and the outer race is revealed in FIGS. 6–8; however, when the inner race of the bearing assembly has rotated into a position where its center x approaches maximum spacing from platen 43, a gap or spacing 45 develops between outer race 31 and membrane 40 (FIG. 9). The gap assures that tubing 12 will not be restrained by the bearing assembly from assuming a condition of maximum lumen cross sectional area, and also allows incremental angular advancement of the outer race 31.

Figure 6:
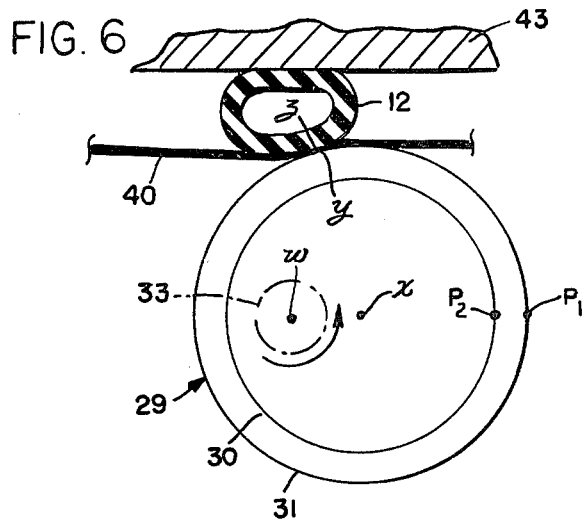
FIGS. 6–9 are schematic views showing the sequence of operation of a modified fluid-pumping apparatus.

The incremental angular advancement may be observed by noting the relative positions of reference points $P_1$ and $P_2$ along the outer and inner races. In FIG. 6, such points are shown to be in radial alignment. As the drive shaft rotates 90° about axis w, reference point $P_2$ has shifted 90° in a counterclockwise direction while $P_1$ retains its original position because rotation of the outer race is resisted by contact with membrane 40. In FIG. 8, points $P_1$ and $P_2$ are 180° apart with $P_1$ still remaining in its original position. However, as the inner race rotates from the position depicted in FIG. 8 towards the position of FIG. 9, the outer race 31 moves out of contact with membrane 40 and the slight frictional resistance inherent in the operation of assembly 29 causes outer race 31 to rotate along with inner race 30. Point $P_1$ therefore shifts a limited angular distance from its original position and will continue such movement until the outer race again contacts membrane 40 in approaching the position of FIG. 6. When the FIG. 6 position is again assumed, however, reference points $P_1$ and $P_2$ will no longer be in radial alignment but will be separated a limited angular distance from each other.

Whether the outer bearing members or races 31 cyclically disengage from the membrane 40 as represented in FIG. 9, or whether they remain in continuous contact with the membrane as previously described, FIGS. 6–8 nevertheless reveal that the portion of the band of tangential contact y associated with each outer bearing member 31 oscillates or shifts slightly from side to side in relation to the longitudinal axis of the tube 12 during operation of the pump apparatus.

FIG. 10 illustrates a construction which is identical to those already described except that membrane 40 has a multiplicity of flexible but non-stretchable reinforcing elements 45 extending along the plane of the membrane in a direction perpendicular to bands of contact y and z. The embedded filaments may be formed of Dacron, wire, or any other suitable material, and prevent lateral stretching of the membrane without appreciably affecting expansion and contraction of the membrane in the general direction of the lines of contact. The preferential reinforcement of the membrane insures that frictional resistance inherent in the construction of bearing assemblies will not in any case be transmitted through the membrane to cause lateral displacement of tube 12 and possible variation in the delivery rate of the pump apparatus. Such reinforcement, while generally unnecessary, may become important in pumps of larger capacity in which the tubing is relatively large (e.g., more than 1 cm. OD) and of substantial wall thickness.

In the operation of the embodiments of FIGS. 1–10, rotation of shaft 33 causes a progressive occlusion of the tube 12 in a downward direction as each bearing assembly in downward sequence assumes the tube-collapsing position depicted in FIG. 4. (It will be understood that if the direction of shaft rotation were reversed, the progressive action of the bearing assemblies would similarly be reversed to drive a segment of fluid upwardly rather than downwardly.) FIG. 3 shows the uppermost bearing assembly of the series in the tube-occluding position of FIG. 4. The next tube bearing assembly directly below it is advancing into occluding positions, the middle assembly is in its maximally open position of FIG. 5, and the remaining three bearing assemblies therebelow are progressing towards their maximally open positions. A metered segment of fluid is thereby forced downwardly through the tube in the direction of peristaltic action.

FIGS. 11–15 depict a preferred embodiment of the invention similar to the embodiments already described except that tube 112 is part of a replaceable cassette 100. If the apparatus is to be used for the administration of parenteral fluids, then the cassette may include a suitable coupling 113 at one end of the tube, the coupling being equipped with a spike and drip chamber as previously indicated, and the upper portion of the tube also being equipped (if desired) with a control device 116 similar to device 16. The opposite end of the tube is provided with a suitable connector 117 which, if the apparatus is to be used for parenteral administration, would take the form of a needle or cannula.

The mid-portion of tube 112 is stretched slightly across the opening 150 of a rigid perimetric frame 151. The frame is generally planar and may be provided with inner and outer flanges 152 and 153 for increased rigidity. To facilitate mounting the tube 112 upon the frame 151, the tube may be formed in sections, with mid-section 112a having its ends secured to rigid mounting sleeves 154 and 155. The sleeves are provided with wing portions 156 that are permanently secured by heat sealing, fusion bonding, or any other suitable means to the portions of frame 151 above and below window opening 150. The upper section 112b of the elastomeric tubing has its lower end secured to the rigid sleeve 154, and the lower section of the tube has its upper end similarly secured to lower sleeve 155.

Figure 11:
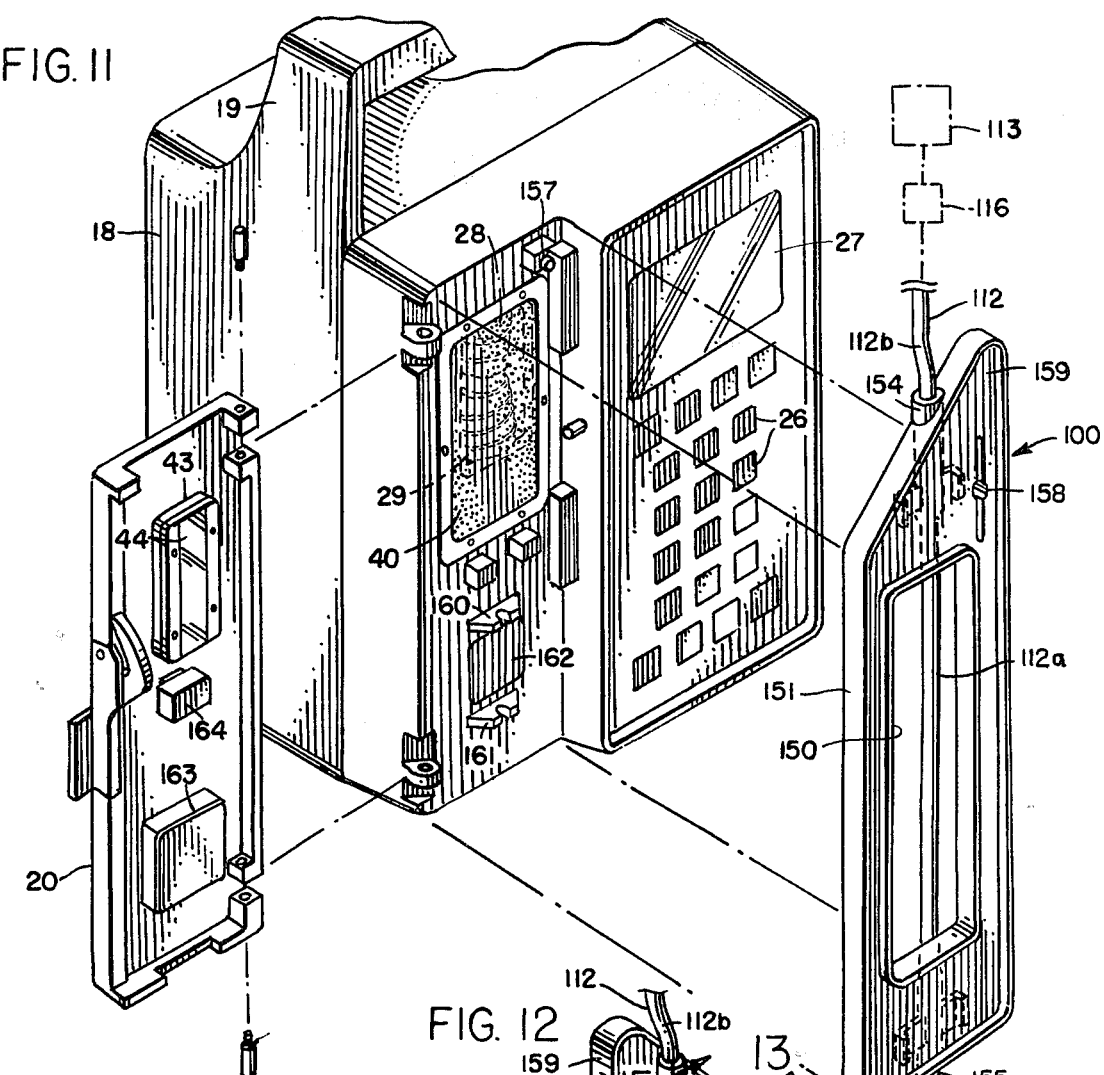
FIG. 11 is a fragmentary perspective view of a pump apparatus modified to utilize a replaceable casette for supporting the fluid delivery tube.

As shown in FIG. 11, platen 43 and facing 44 are mounted on door panel 20 and are dimensioned to extend through opening 150 of cassette frame 151 when the cassette is in operative position and the door is latched closed. When the cassette is in operating position, locating pin 157 of the housing extends through aperture 158 in the upper portion of the frame 151. Tube section 112a engages membrane 28 and is supported or braced by planar platen 43 and its resilient facing 44 in the same manner as shown and described with respect to FIGS. 3–10. However, the cassette 100 greatly facilitates use of the apparatus, particularly in medical applications, because it may be discarded in its entirety after it has served its purpose, and a new sterile cassette may be inserted into position for use by the same patient or a different patient, without risks of cross contamination and without need to clean and sterilize the used cassette or the pump housing and mechanism.

The ease and speed with which a cassette may be removed and replaced is of course of considerable importance, especially in medical applications where time may be critical. The cassette also insures accurate alignment of the tensioned section 112a of the tube with respect to the rotational axis w of the drive shaft, a critical relationship as previously described in connection with FIGS. 3–10. Furthermore, the cassette 100 allows precise tensioning or stretching of the linear tube section 112a during manufacture of the cassette. Since the extent of tensioning of the linear tube section affects the internal diameter of that section, reproducibility of flow rates may be assured.

In assembling the cassette of this invention it has been found advantageous to perform the following steps to assure uniform stretching of tube section 112a. The tubing is first connected to sleeves 156 before the sleeves are attached to perimetric frame 151. The frame is mounted on a jig (not shown) utilizing the alignment aperture 158. The jig accommodates two conventional ultrasonic welding horns, and one of the horns is operated to weld one of the sleeves 156 to the frame. A weight capable of exerting a predetermined stretching force is attached to the other end of the tubing and the tubing is freely stretched by the weight. The other attachment sleeve 156, which has been connected to the tubing but has been allowed to float freely with regard to the frame, is then secured to the frame by the second ultrasonic welder. Accurate "inline" measurement of tubing inside and outside diameters is possible by means of laser micrometers, air gauges, or the like. If a deviation is detected then the extent of stretching may be readily adjusted by varying the weight used to produce such stretching. By such a procedure, stretching, tubing size, and pumping action may be accurately controlled. While ultrasonic welding has been found particularly effective, other means of attachment such as cementing, solvent bonding, or mechanical fastening may be used.

Should production operations result in variations in the inside diameters of the tensioned tube sections 112a of the cassettes and not be corrected by stretching adjustment as described above, each cassette may be coded with suitable indicia, colors, or indentations on the frame 151 or elsewhere to indicate the average ID of the tensioned tubular pumping section 112a of that particular cassette, and the microprocessor of the pump mechanism may then be programmed accordingly to correct the pump speed to achieve the required delivery rate. If desired, the pump may be equipped with mechanical or electrooptical transducers for reading such coding automatically.

The frame 151 of the cassette includes a tab portion 159 which projects beyond the door 20 when the door is closed and the cassette is in operative position, thereby providing a clear visual indication that a cassette is in place. In addition, tab portion 159 is easily gripped by a user to facilitate insertion and removal of a cassette.

Depending on its intended use, the system may include safety functions to insure that unintended interruptions or changes in pump operation will not occur or at least will not pass undetected. For such purposes, the opening 150 in the cassette frame, and the tensioned pump section 112a of the tube, are substantially longer than the series of bearing assemblies 29. When the cassette is in place, the lower portion of tube section 112a bridges a pair of guides 160, 161 and extends between the emitter 162 and receiver 163 of an ultrasonic or photoptic bubble detector. Also, an occlusion detector 164 may contact a portion of the tube directly below, or on the discharge side, of the series of rotor bearing pump assemblies 29 to sense increases in back pressure that might be caused by kinking of the outlet section 112c of the tube, obstruction of needle 117, or any other reason. Since bubble detectors and pressure sensors are well known in the art and do not constitute elements of this invention, further discussion is believed unnecessary herein.

The rigid platen 43, resilient facing 44, and elastomeric tube 12 and 112a are all preferably formed of materials that have suffficient transparency to permit a user or operator to view the peristalsis of the tube and the movement of fluid therethrough through the platen. For that purpose, the platen 43 may be formed of glass or any rigid and adequately transparent polymeric material such as polymethyl methacrylate, polymethyl alphachloro acrylate, cyclohexyl methacrylate, and the like. The facing layer 44 and tube 12 and 112a are preferably formed of silicone rubber or polyurethane rubber, but any elastomeric material having similar properties may be used. The elastomeric material of membranes 40 and 40' may also be silicone rubber or polyurethane rubber but, since transparency of the membrane is not necessary, a variety of other elastomeric materials such as neoprene may be utilized.

Figure 12:
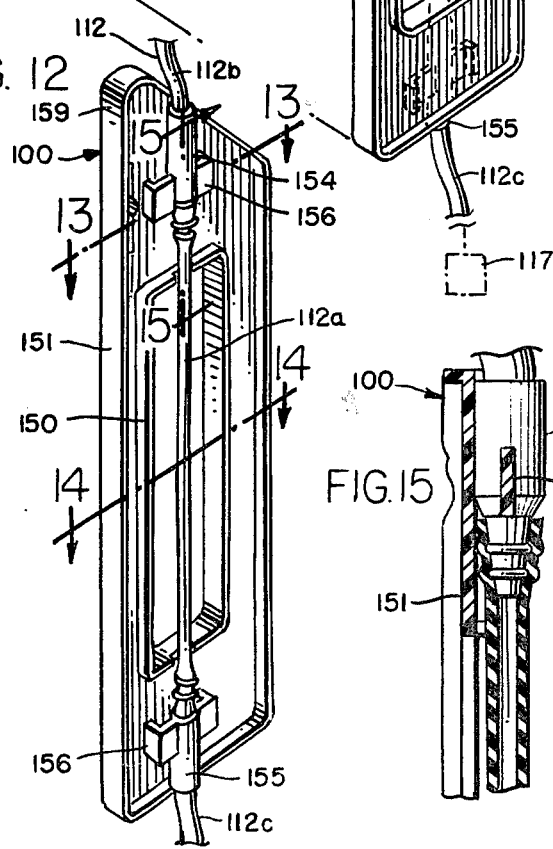
FIG. 12 is a perspective view showing the opposite side of the casette depicted in FIG. 11.

Although the pump apparatus has been described for use in the administration of parenteral fluids, it is by no means limited to such use. FIG. 12 illustrates essentially the same linear peristaltic pumping system used for wound drainage. A perforated catheter 217 is located at the wound site to collect exudate, and elastomeric tube 212, similar to but preferably of larger ID than tubes 12 and 112, leads from the catheter to fluid container 214. The tensioned linear section of the tube extends through pump casing 218 where it is engaged by elastomeric membrane 240 and the resilient facing 244 of rigid platen 243, all as previously described. A series of eccentric bearing assemblies 229 driven by a battery operated motor 224 engages the membrane and causes peristaltic metered flow through tube 212. In all major respects the pump apparatus is the same as previously described in connection with FIGS. 1–11; however, the system of FIG. 12 should include a sensor 280 for detecting when drainage from the wound is less than the flow rate of the pump. Such a sensor may be in the form of a vacuum switch for sensing collapse of the tube on the upstream side of the pump mechanism, the switch being electrically coupled to the motor 224 to stop the pump at a predetermined suction value. As the exudate again fills the line on the extreme side of the pump, the vacuum switch restarts the pump motor and the cycle repeats itself.

Figure 13:
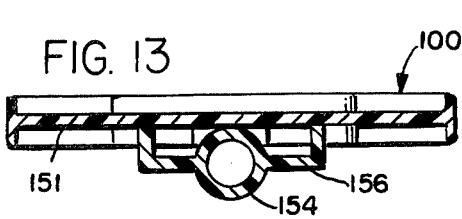
FIG. 13 is an enlarged cross sectional view taken along line 13—13 of FIG. 12.
Figure 14:
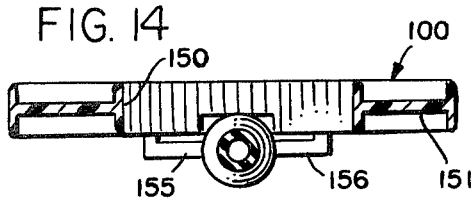
FIG. 14 is an enlarged sectional view along line 14—14 of FIG. 12.
Figure 15:
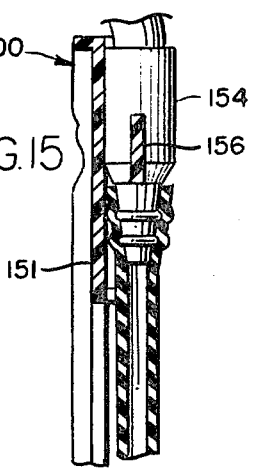
FIG. 15 is an enlarged longitudinal sectional view along line 15—15 of FIG. 12.
Figure 16:
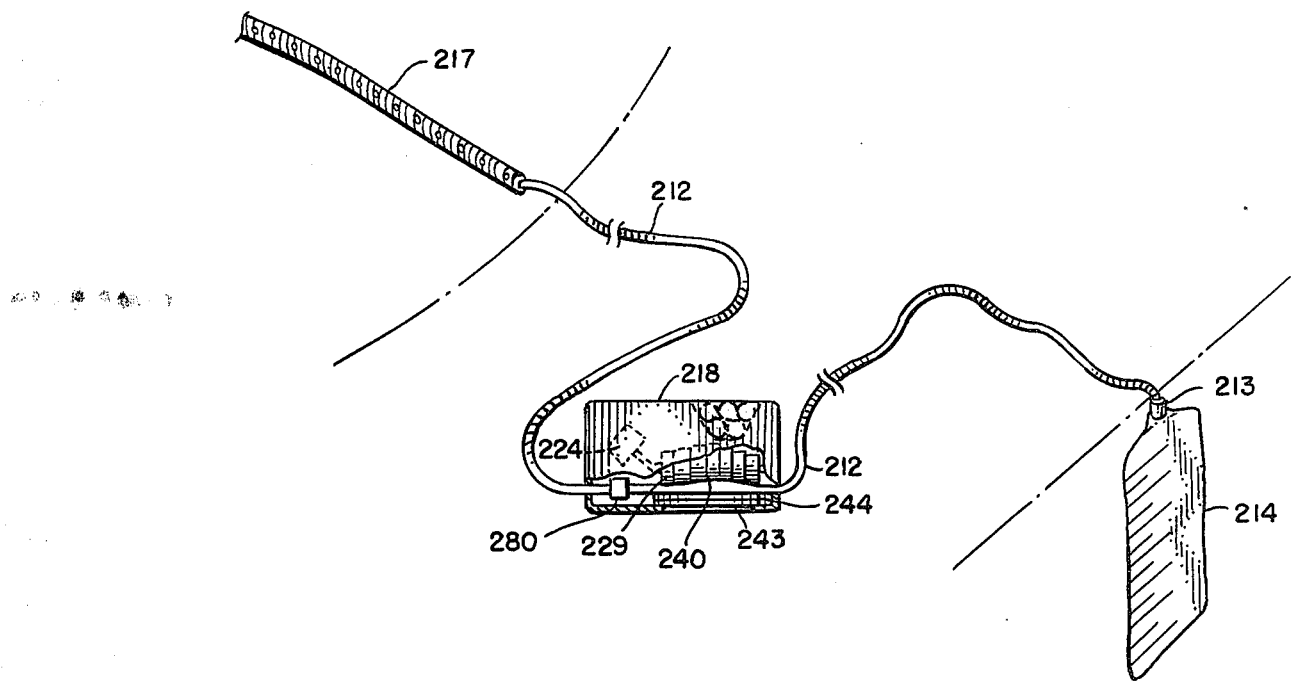
FIG. 16 illustrates a pump embodying the invention utilized in a system for wound drainage.
Figure 17:
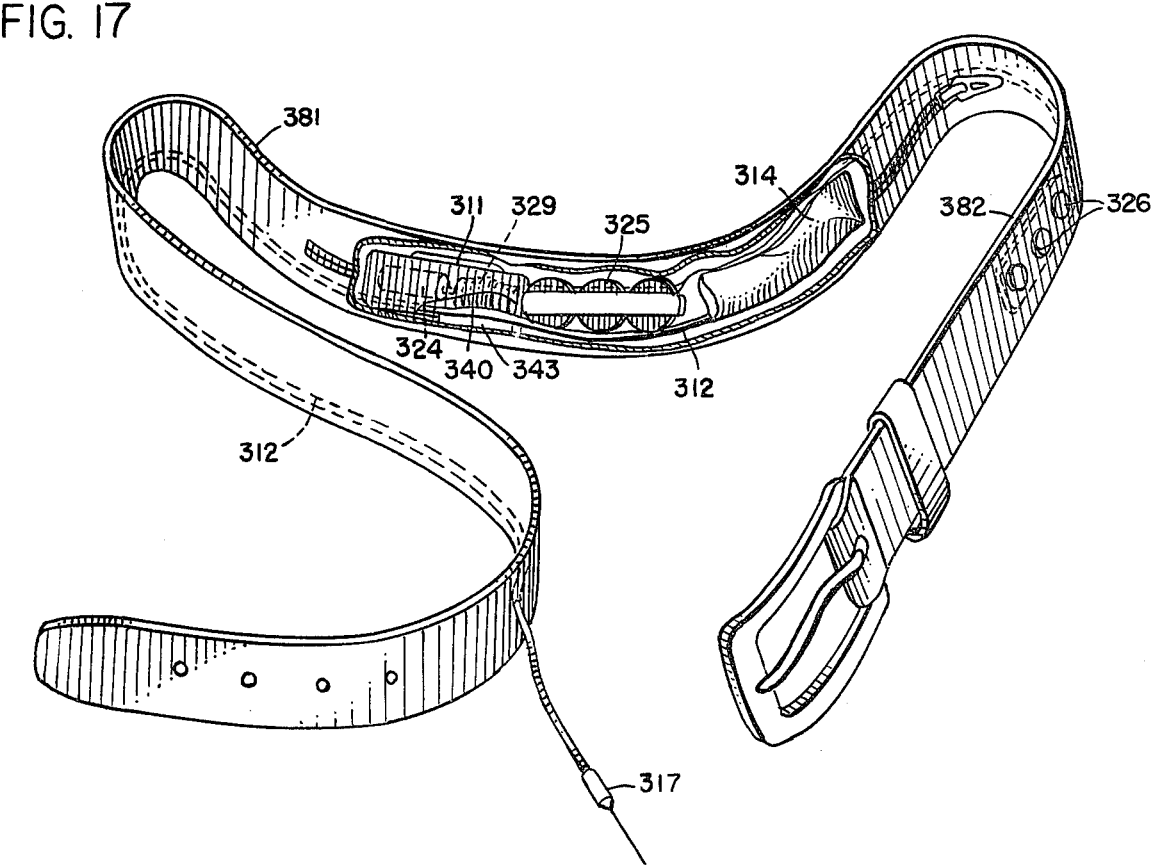
FIG. 17 depicts a pump embodying the invention as one component of a combination of elements for continuous infusion of a drug over an extended period.

FIG. 13 schematically depicts an infusion system in which the pump apparatus of the invention is miniaturized to such an extent that the pump 311 with its series of eccentric bearings 329 driven by motor 324 (and connected thereto by a highly flexible coupling), as well as batteries 325, container or reservoir 314, resilient tube 312, platen 343 with its resilient facing, and membrane 340 are all housed within a belt 381. The outlet end portion of the elastomeric tube is provided with a connector 317 in the form of a hypodermic needle or cannula. Electrical control of the operation of the pump is provided by controller 382 equipped with control buttons 326. Continuous patient-controlled administration of insulin to a diabetic patient, or other therapeutic agents to patients requiring such treatment, is thereby achieved. While the system is depicted as being housed in a belt 381, such an enclosure is illustrated primarily to show the extent of miniaturization possible for a system embodying the invention.

While in the foregoing embodiments of the invention have been disclosed in considerable detail for purposes of illustration, it will be understood by those skilled in the art that many of these details may be varied without departing from the spirit and scope of the invention.

I claim:

1. A peristaltic pump apparatus comprising a series of bearing assemblies each having concentric inner and outer bearing members freely rotatable with respect to each other; a drive shaft; said inner members of said bearing assemblies being eccentrically mounted upon said drive shaft with the centers of said inner members being equidistant from the axis of said drive shaft and spaced uniform angular distances thereabout to describe a helix about said axis; journal means rotatably supporting said drive shaft; power means for rotating said drive shaft; an elastomeric membrane alongside said series of bearing assemblies; means supporting said membrane for tangential engagement with said outer members along a first band of contact on one side of said membrane; a straight, elongated elastomeric tube extending along and engaging the opposite side of said membrane along a second band of contact directly opposite from said first band of contact; and platen means for supporting said tube with the longitudinal axis thereof in spaced parallel relation with respect to the rotational axis of said drive shaft and in engagement with said membrane along said second band of contact; that portion of said first band of contact associated with each outer member oscillating from side to side in relation to said longitudinal axis of said tube when said apparatus is in operation.

2. The apparatus of claim 1 in which said inner member of each bearing assembly has its center movable, as said shaft is rotated, between one extreme position wherein said center is spaced maximally from the longitudinal axis of said tube and the lumen of said tube is substantially fully open and another extreme position wherein said center is spaced minimally from the longitudinal axis of said tube and said lumen is substantially closed.

3. The apparatus of claims 1 or 2 in which said first and second bands of contact and said axis of said drive shaft all lie along the same plane.

4. The apparatus of claim 3 in which said inner and outer members constitute inner and outer races, respectively, of said bearing assemblies, and anti-friction bearing elements are provided between said inner and outer races.

5. The apparatus of claim 3 in which said inner and outer members of each of said bearing assemblies slidably engage each other.

6. The apparatus of claim 3 in which said membrane and tube are disposed in frictional non-slipping engagement with each other.

7. The apparatus of claim 3 in which said outer members and said membrane are in frictional non-slipping engagement with each other.

8. The apparatus of claim 3 in which said platen means comprises a rigid support plate.

9. The apparatus of claim 8 in which said support plate is transparent.

10. The apparatus of claim 9 in which a facing of resilient material extends along said plate in contact with said tube.

11. The apparatus of claim 10 in which said facing material is transparent.

12. The apparatus of claim 3 in which said membrane includes a multiplicity of spaced, flexible, and substantially non-stretchable reinforcing elements extending along the plane of the membrane in a direction perpendicular to said lines of contact.

13. The apparatus of claim 12 in which said reinforcing elements are flexible and substantially non-stretchable filaments embedded in said membrane.

14. The apparatus of claim 3 in which said tube includes end sections extending substantial distances in opposite directions beyond said series of bearing assemblies; container means connected to and communicating with one of said end sections of said tube; and connecting means joined to and communicating with the other of said end sections for connecting said tube to a patient.

15. The apparatus of claim 14 in which said drive shaft is rotated by said power means to direct fluid flow from said container means towards said connecting means; said container means comprising a fluid reservoir containing a sterile fluid for patient administration; said connecting means comprising a cannula for infusing and administering said fluid to a patient.

16. The apparatus of claim 14 in which said drive shaft is rotated by said power means to direct fluid flow from said connecting means to said container means; said container means comprising a reservoir for receiving a body fluid; said connecting means comprising a catheter for receiving body fluid from a patient.

17. The apparatus of claim 16 in which sensing means is provided for detecting collapse of said one end section of said tube between said catheter and said bearing assemblies; said sensing means being operatively connected to said power means for interrupting operation of said power means while said tube section is collapsed.

18. The apparatus of claim 3 in which said outer member of each bearing assembly is in continuous engagement with said membrane along said first band of contact during operation of said apparatus.

19. The apparatus of claim 3 in which said outer member of each bearing assembly is momentarily disengaged from said membrane when said inner member thereof is in said one extreme position.

20. The apparatus of claim 1 in which said elastomeric tube is transparent.

21. The apparatus of claim 1 in which the number of bearing assemblies in said series falls within the range of 3 to 30 per 360° helical turn.

22. A portable linear peristaltic pump apparatus comprising a series of bearing assemblies each having an inner race, an outer race, and anti-friction bearing elements therebetween; a drive shaft; said inner races of said bearing assemblies being eccentrically mounted upon said drive shaft with the centers of said inner races being equidistant from the axis of said drive shaft and spaced uniform angular distances thereabout to describe a helix about said axis; journal means rotatably supporting said drive shaft; power means for rotating said drive shaft; an elastomeric membrane alongside said series of bearing assemblies; means supporting said membrane for tangential engagement with said outer races along a first band of contact on one side of said membrane; a straight elongated elastomeric tube having a mid-section extending along and engaging the opposite side of said membrane along a second band of contact directly opposite from said first band of contact; means engaging and supporting said tube to maintain said mid-section thereof in stretched and tensioned condition; and platen means engaging and bracing said tensioned mid-section of said tube with the longitudinal axis thereof in parallel relation with respect to the rotational axis of said drive shaft and in engagement with said membrane along said second band of contact; that portion of said first band of contact associated with said outer race of each bearing assembly oscillating from side to side in relation to said longitudinal axis of said tube when said apparatus is in operation.

23. The apparatus of claim 22 in which said first and second bands of contact and said axis of said drive shaft all lie along substantially the same plane.

24. The apparatus of claim 23 in which said inner race of each bearing assembly has its center movable, as said drive shaft is rotated, between one extreme position wherein said center is spaced maximally from the longitudinal axis of said mid-section of said tube and the lumen of said tube is substantially fully open and another extreme position wherein said center is spaced minimally from the longitudinal axis of said mid-section of said tube and said lumen is substantially closed.

25. The apparatus of claim 24 in which said outer race of each bearing assembly is in continuous engagement with said membrane along said first band of contact during operation of said apparatus.

26. The apparatus of claim 24 in which said outer race of each bearing assembly is momentarily disengaged from said membrane when said inner race is in said one extreme position.

27. The apparatus of claim 22 in which said platen comprises a rigid planar support plate.

28. The apparatus of claim 27 in which said support plate is transparent.

29. The apparatus of claim 27 in which a facing of resilient material extends along said support plate in contact with said mid-section of said tube.

30. The apparatus of claim 29 in which said facing material is transparent.

31. The apparatus of claim 28 in which said mid-section of said tube is transparent.

32. The apparatus of claim 22 in which said membrane includes a multiplicity of spaced, flexible, and substantially non-stretchable reinforcing elements extending along the plane of the membrane in a direction perpendicular to said lines of contact.

33. The apparatus of claim 22 in which said tube also includes a pair of end sections at opposite ends of said mid-section; container means connected to and communicating with one of said end sections; and connecting means joined to and communicating with the other of said end sections for connecting said tube to a patient.

34. The apparatus of claim 33 in which said drive shaft is rotated by said power means to direct flow from said container means towards said connecting means; said container means comprising a fluid reservoir containing a sterile fluid for patient administration; said connecting means comprising a cannula for fluid administration to a patient.

35. The apparatus of claim 33 in which said drive shaft is rotated by power means to direct fluid flow from said connecting means to said container means; said container means comprising a reservoir for receiving a body fluid; said connecting means comprising a catheter for receiving body fluid from a patient.

* * * * *